(12) United States Patent
Sugiyama

(10) Patent No.: US 9,975,452 B2
(45) Date of Patent: May 22, 2018

(54) SEAT HAVING CAPACITIVE COUPLING SENSOR

(71) Applicant: TS TECH CO., LTD., Asaka-shi, Saitama (JP)

(72) Inventor: Shinji Sugiyama, Tochigi (JP)

(73) Assignee: TS Tech Co., Ltd., Saitama (JP)

( * ) Notice: Subject to any disclaimer, the term of this patent is extended or adjusted under 35 U.S.C. 154(b) by 129 days.

(21) Appl. No.: 14/916,672

(22) PCT Filed: Sep. 5, 2014

(86) PCT No.: PCT/JP2014/073553
§ 371 (c)(1),
(2) Date: Mar. 4, 2016

(87) PCT Pub. No.: WO2015/034065
PCT Pub. Date: Mar. 12, 2015

(65) Prior Publication Data
US 2016/0200220 A1  Jul. 14, 2016

(30) Foreign Application Priority Data
Sep. 5, 2013  (JP) .................................. 2013-184095

(51) Int. Cl.
*G01R 27/08* (2006.01)
*B60N 2/00* (2006.01)
(Continued)

(52) U.S. Cl.
CPC .......... *B60N 2/002* (2013.01); *A61B 5/04085* (2013.01); *A61B 5/04284* (2013.01);
(Continued)

(58) Field of Classification Search
CPC .. B60N 2/002; B60N 2002/0268; B60N 2/28; B60N 2/5685; B60N 2002/0272;
(Continued)

(56) References Cited

U.S. PATENT DOCUMENTS 7,317,392 B2 *  1/2008  DuRocher ......... B60R 21/01532
                                                 280/734
8,269,512 B2 *  9/2012  Ootaka ................. B60N 2/002
                                                 297/217.3
(Continued)

FOREIGN PATENT DOCUMENTS

JP       2003-070774 A    3/2003
JP       2005-110801 A    4/2005
(Continued)

OTHER PUBLICATIONS

Extended European Search Report issued in related application EP 14842534.1, dated Jul. 29, 2016, 10 pages.
(Continued)

*Primary Examiner* — Vinh Nguyen
(74) *Attorney, Agent, or Firm* — Drinker Biddle & Reath LLP

(57) ABSTRACT

A seat configured so that the accuracy of detection of each sensor provided in the seat to detect the body potential of a seated occupant can be improved without degrading the sense and comfort of the seat. A seat includes a trim cover having a contact surface for a seated occupant, and sensors arranged opposite to the contact surface and configured to detect the body potential of the seated occupant. Each sensor is a capacitive coupling sensor configured to detect the body potential through the trim cover. Moreover, a portion of the seat facing each sensor includes a dielectric configured to increase the dielectric constant of such a portion.

20 Claims, 6 Drawing Sheets

(51) Int. Cl.
    *B60N 2/58*      (2006.01)
    *A61B 5/00*      (2006.01)
    *A61B 5/0408*    (2006.01)
    *A61B 5/0428*    (2006.01)

(52) U.S. Cl.
    CPC .............. *A61B 5/6893* (2013.01); *B60N 2/58* (2013.01); *A61B 2562/0214* (2013.01); *A61B 2562/125* (2013.01)

(58) Field of Classification Search
    CPC .... B60N 2/0276; B60N 2/4829; B60N 2/015; B60N 2/0248; B60N 2/067; B60N 2/4852; B60N 2/4885; B60N 2/0244; B60N 2/0252; B60N 2/86; B60N 2/66; B60N 2/0224; B60N 2/5678; B60N 2/02; B60N 2/2884; B60N 2205/40; B60N 2/028; B60N 2/0732; B60N 2/18; B60N 2/1803; B60N 2/482; B60N 2/485; B60N 2/4864; B60N 2/5635; B60N 2/58; B60N 2/68; B60R 21/01532; B60R 21/01516; B60R 21/0152; B60R 21/01536; B60R 21/0153; B60R 21/01542; B60R 21/01552; B60R 21/01554; B60R 2021/0027; B60R 21/0132; B60R 21/01544; B60R 16/037; B60R 2001/122; B60R 2021/01315; B60R 2022/288; B60R 21/0136; B60R 25/25; B60R 21/0154; B60R 2022/4825; B60R 21/01526; B60R 22/20; B60R 21/01512; B60R 2022/4816; B60R 2022/4858; B60R 2021/0037; B60R 21/233; B60R 2001/1223; B60R 21/2338; B60R 25/00; G01D 5/2405; G01L 1/142; A61B 2562/0214; A61B 5/04085; A61B 5/04284; A61B 5/6893
    See application file for complete search history.

(56) References Cited

U.S. PATENT DOCUMENTS

| | | | | |
|---|---|---|---|---|
| 2001/0045733 A1* | 11/2001 | Stanley | ............... | B60N 2/002 280/735 |
| 2006/0066085 A1 | 3/2006 | DuRocher | | |
| 2007/0010750 A1 | 1/2007 | Ueno et al. | | |
| 2008/0001253 A1* | 1/2008 | Mosley | ............... | H01G 4/232 257/532 |
| 2008/0186192 A1* | 8/2008 | Yamanaka | ............... | B60N 2/002 340/667 |
| 2011/0074447 A1* | 3/2011 | Ootaka | ............... | B60N 2/002 324/679 |
| 2012/0006147 A1 | 1/2012 | Sano | | |
| 2012/0056631 A1 | 3/2012 | Feddes et al. | | |
| 2012/0101326 A1 | 4/2012 | Simon et al. | | |
| 2012/0265080 A1 | 10/2012 | Yu et al. | | |

FOREIGN PATENT DOCUMENTS

| | | |
|---|---|---|
| JP | 2009-050679 A | 3/2009 |
| JP | 2009-106674 A | 5/2009 |
| JP | 2009-261735 A | 11/2009 |
| JP | 2012-020002 A | 2/2012 |
| JP | 2012-527940 A | 11/2012 |
| JP | 2013-212311 A | 10/2013 |
| WO | 02/065904 A1 | 8/2002 |
| WO | 02/065905 A1 | 8/2002 |
| WO | 03/048789 A2 | 6/2003 |
| WO | 2005/032368 A1 | 4/2005 |

OTHER PUBLICATIONS

Heuer et al., "Unobtrusive In-Vehicle Biosignal Instrumentation for Advanced Driver Assistance and Active Safety," 2010 IEEE EMBS Conference on Biomedical Engineering & Sciences (IECBES 2010), Kuala Lumpur, Malaysia, Nov. 30, 2010, pp. 252-256.
Walter et al., "The smart car seat: personalized monitoring of vital signs in automotive applications," Personals and Ubiquitous Computing, Springer Verlag, LO, vol. 15(7), Jan. 7, 2011, pp. 707-715.
Office Action issued in related application JP 2015-535535, dated Mar. 27, 2018, with machine generated English language translation, 9 pages.

\* cited by examiner

SEAT HAVING CAPACITIVE COUPLING SENSOR

CROSS REFERENCE TO RELATED APPLICATIONS

This application is a National Stage Entry application of PCT Application No. PCT/JP2014/073553, filed Sep. 5, 2014, which claims the priority benefit of Japanese Patent Application No. 2013-184095, filed Sep. 5, 2013, the contents of each of which are incorporated herein by reference in their entireties.

BACKGROUND

Disclosed herein is a seat, and particularly a seat including sensors configured to detect the body potential of an occupant when the occupant is seated.

A configuration has been already known, in which sensors configured to detect the body potential of a seated occupant to monitor the health and wakefulness of the seated occupant are attached to a seat. For example, JP 2009-50679A discloses a configuration in which electrode sensors are embedded in a cover of a backrest of a driver's seat to measure the heart rate of a driver of an automobile.

The above-described electrode sensor is a sensor, i.e., a capacitive coupling sensor, capable of detecting the body potential through clothes of the driver and the cover member of the seat without contacting the skin of the driver. In the configuration of JP 2009-50679A, these sensors can be used to detect a weak signal from the heart of the driver while the driver is seated on the seat. The sensors disclosed in JP 2009-50679A provide an electrocardiographic measurement device suitable for mounting on a vehicle.

The electrostatic capacitance between an electrode sensor and the skin of the subject (such as the driver) is greatly influenced by the detection accuracy of the body potential, and a lower electrostatic capacitance generally results in a lower detection accuracy. Moreover, the space between the skin of the subject and each electrode sensor might change due to, e.g., a change in the posture of the driver and vibration of the vehicle while the vehicle is running. Accordingly, the above-described electrostatic capacitance changes due to such a change in space.

The size of the electrode sensor, particularly the area of a potential detection surface, might be increased to address the above-described problem. However, when the sensors are placed and embedded in the seat, the area of the potential detection surface cannot be easily increased due to installation space limitations.

At the same time, it is important that the quality of the seat, particularly the sense of seating on the seat (i.e., the comfortability on the seat), is maintained.

SUMMARY

In an embodiment, there is a seat configured so that the accuracy of detection of each sensor provided in the seat to detect the body potential of a seated occupant can be improved without degrading the sense or comfort of the seat.

According to an embodiment, a seat includes a cover member having a contact surface for a seated occupant, and a sensor disposed opposite to the contact surface and configured to detect, when the occupant is seated, the body potential of the seated occupant, and to output a signal corresponding to the body potential. The sensor is a capacitive coupling sensor configured to detect the body potential through the cover member, and a portion of the seat facing the sensor includes a dielectric configured to increase a dielectric constant of the portion.

Since the portion of the seat facing the sensor includes the dielectric configured to increase the dielectric constant of such a portion in the seat configured as described above, the electrostatic capacitance between the sensor and the skin of the seated occupant increases. As a result of increasing the electrostatic capacitance, the accuracy in detection of the body potential of the seated occupant by the sensor is improved. Since the above-described dielectric is provided in the seat, the influence of the dielectric on the sense and comfort of seating on the seat is reduced. While the sense and comfort of the seating on the seat is maintained, the detection accuracy of the sensor can be improved.

In the above-described seat, an application agent containing the dielectric may be applied onto at least part of the surface of the sensor facing the cover member to form an application agent layer. Alternatively, a film containing the dielectric may be attached to at least part of the surface of the sensor facing the cover member.

In the above-described configuration, the portion (the application agent layer and the film) including the dielectric is directly provided on the surface of the sensor, and is integrated with the sensor. According to such a configuration, the flexibility (specifically the followability to a load acting on the sensor when the seated occupant leans on the seat) of the sensor is higher as compared to the configuration in which a portion including a dielectric is separated from a sensor.

In the above-described seat, the dielectric may be contained across the entirety of a portion of the cover member facing the sensor. With the above-described configuration, the dielectric may be contained across the entirety of the portion of the cover member facing the sensor, and therefore, the electrostatic capacitance between the skin of the seated occupant and the sensor further increases. This can further improve the detection accuracy of the sensor.

In the above-described seat, the cover member may include a covering material forming the contact surface, and a wadding material attached to the surface of the covering material opposite to the contact surface and that the dielectric is contained in at least part of a portion of the wadding material facing the sensor. When the dielectric is contained in the wadding material of the cover member as in the above-described configuration, the dielectric can be easily contained, and therefore, the detection accuracy of the sensor can be more easily improved.

In the above-described seat, the wadding material may be formed of a foam material formed with air bubbles communicating with each other. When the air bubbles formed in the wadding material are air bubbles communicating with each other as in the above-described configuration, the dielectric is easily contained in the air bubbles, and the content of the dielectric is relatively high. Thus, the detection accuracy of the sensor can be more easily improved.

In the above-described seat, an attachment member containing the dielectric may be attached to at least part of the portion of the cover member facing the sensor. When the attachment member containing the dielectric is, as in the above-described configuration, attached to the above-described facing portion to increase the electrostatic capacitance at the portion of the cover member facing the sensor, the electrostatic capacitance can be increased with a simpler configuration. Further, when the attachment member is freely detachable, the attachment member can be easily replaced.

In the above-described seat, the attachment member may be made of silicon rubber and that at the outer edge of the attachment member, at least one cutout is formed to extend inward from the outer edge. When the cutout is formed at the outer edge of the attachment member made of the silicon rubber as in the above-described configuration, if the cover member is bent due to the seated occupant's back leaning on the seat, the attachment member can be easily bent to follow bending of the cover member. That is, the attachment member made of the silicon rubber flexibly deforms under the load acting every time the back of the seated occupant leans on the seat, and as a result, the durability against such a load can be improved.

In the above-described seat, the sensor may be a sheet sensor and that the surface size of the portion of the seat including the dielectric on the side facing the sensor is equal to or larger than the surface size of the sensor on the side facing the cover member. When the size of the portion of the seat including the dielectric is equal to or larger than the size of the sensor as in the above-described configuration, the electrostatic capacitance between the sensor and the skin of the seated occupant can be effectively increased. As a result, the accuracy in detection of the body potential of the seated occupant by the sensor is further improved.

In the above-described seat, the sensor may include a plurality of arranged sensors and the portion of the seat including the dielectric may face at least two of the sensors and is continuously provided. When the portion of the seat including the dielectric faces, as in the above-described configuration, at least two of the sensors and is continuously provided, the portion including the dielectric is provided as a united portion. Thus, such a portion can be more easily provided.

In the above-described seat, the dielectric may be titanium oxide or barium titanate. The titanium oxide or the barium titanate is effective as the dielectric. Thus, when the dielectric is contained in at least part of the portion of the cover member facing each sensor, the electrostatic capacitance between the skin of the seated occupant and each sensor increases. As a result, the detection accuracy of the sensors can be improved.

When the above-described seat is a vehicle seat mounted on a vehicle, the advantageous effects of the seat are more effectively exhibited. Specifically, due to a change in the posture of the seated occupant or vibration of the vehicle while the vehicle is running, the electrostatic capacitance between the skin of the seated occupant and each sensor changes in the case of the vehicle seat, as described above. As a result, there is a probability that the electrostatic capacitance decreases. For the vehicle seat, the sense or comfort of the seat is focused as the quality of the seat. For this reason, the advantageous effects of the above-described seat, i.e., maintaining the sense of seating on the seat and improving the detection accuracy of the sensors, become more meaningful.

According to an embodiment, there is provided a seat where the detection accuracy of the sensors is improved while the sense and comfort of seating on the seat is maintained. These advantageous effects are more effectively exhibited in the vehicle seat mounted on the vehicle. Specifically, due to a change in the posture of the seated occupant or vibration of the vehicle while the vehicle is running, the electrostatic capacitance between the skin of the seated occupant and each sensor changes in the case of the vehicle seat. As a result, there is a probability that the electrostatic capacitance decreases. For the vehicle seat, the sense and comfort of seating on the seat is focused as the quality of the seat. For this reason, the advantageous effects of the seat described herein, i.e., the advantageous effects of maintaining the sense of seating on the seat and improving the detection accuracy of the sensors, become more meaningful.

Moreover, according to an embodiment, the application agent layer or the film containing the dielectric is provided on the surface of each sensor to integrate the portion including the dielectric with the sensor. As a result, the flexibility (the followability) of each sensor to the load acting on the sensor when the seated occupant leans on the seat is improved.

Further, according to an embodiment, since the dielectric is contained across the entirety of the portion of the cover member facing each sensor, the electrostatic capacitance between the skin of the seated occupant and the sensor further increases, and therefore, the detection accuracy of the sensors is further improved.

In addition, according to an embodiment, since the dielectric is contained in at least part of the portion of the wadding material of the cover member facing each sensor, the dielectric can be easily contained, and therefore, the detection accuracy of the sensors can be more easily improved.

Moreover, according to an embodiment, since the dielectric is contained in the air bubbles formed in the wadding material and communicating with each other, the dielectric is easily contained, and the content of the dielectric is relatively high. As a result, the detection accuracy of the sensors can be much more easily improved.

Further, according to an embodiment, since the titanium oxide or the barium titanate is used as the dielectric, the electrostatic capacitance between the skin of the seated occupant and each sensor increases, and therefore, the detection accuracy of the sensors can be improved.

In addition, according to an embodiment, since the attachment member containing the dielectric is attached to the above-described facing portion to increase the electrostatic capacitance at the portion of the cover member facing each sensor, the electrostatic capacitance can be increased with a simpler configuration. Further, when the attachment member is freely detachable, the attachment member can be easily replaced.

Moreover, according to an embodiment, the cutout is formed at the outer edge of the attachment member made of the silicon rubber. Thus, when the cover member is bent due to the seated occupant's back leaning on the seat, the attachment member can be easily bent to follow bending of the cover member. As a result, the durability of the attachment member made of the silicon rubber against the load acting every time the back of the seated occupant leans on the seat can be improved.

Further, according to an embodiment, since the size of the portion of the seat including the dielectric is equal to or larger than the size of the sensor, the electrostatic capacitance between each sensor and the skin of the seated occupant can be effectively increased. As a result, the accuracy in detection of the body potential of the seated occupant by the sensors can be further improved.

In addition, according to an embodiment, since the portion of the seat including the dielectric faces at least two of the sensors and is continuously provided, the portion including the dielectric is provided as a united portion. Thus, such a portion can be more easily provided.

DESCRIPTION OF EMBODIMENTS

A seat S according to an embodiment will be described below with reference to drawings. The seat S is a vehicle seat mounted on a vehicle, and is mainly used as a driver's seat. Note that the application of the seat S is not limited to the driver's seat, and the seat S may be used as a jump-seat or a backseat.

Figure 1:
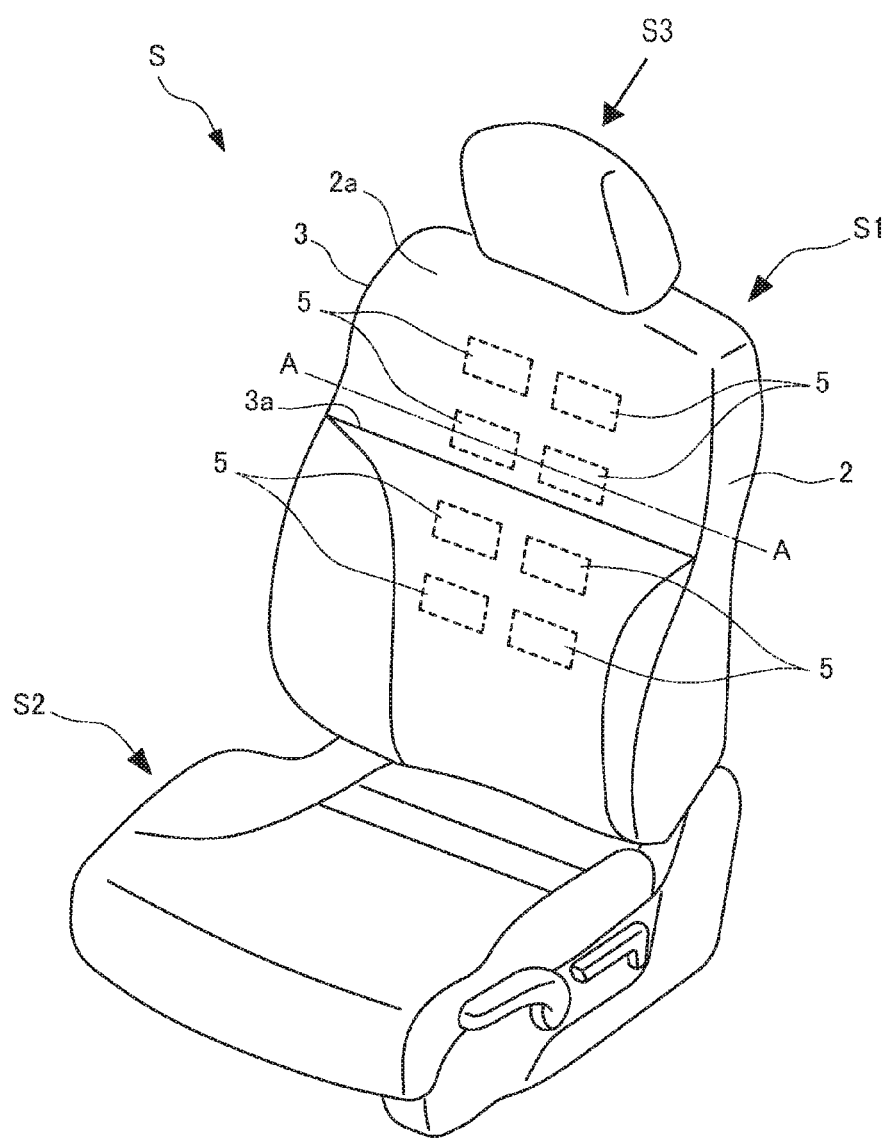
FIG. 1 is an external view of a seat according to an embodiment.

The seat S has an outer appearance as illustrated in FIG. 1, and the structure thereof is similar to that of a well-known vehicle seat, except for a wadding material 4 and a sensor 5 described later. FIG. 1 is an external view of the seat S.

Figure 2:
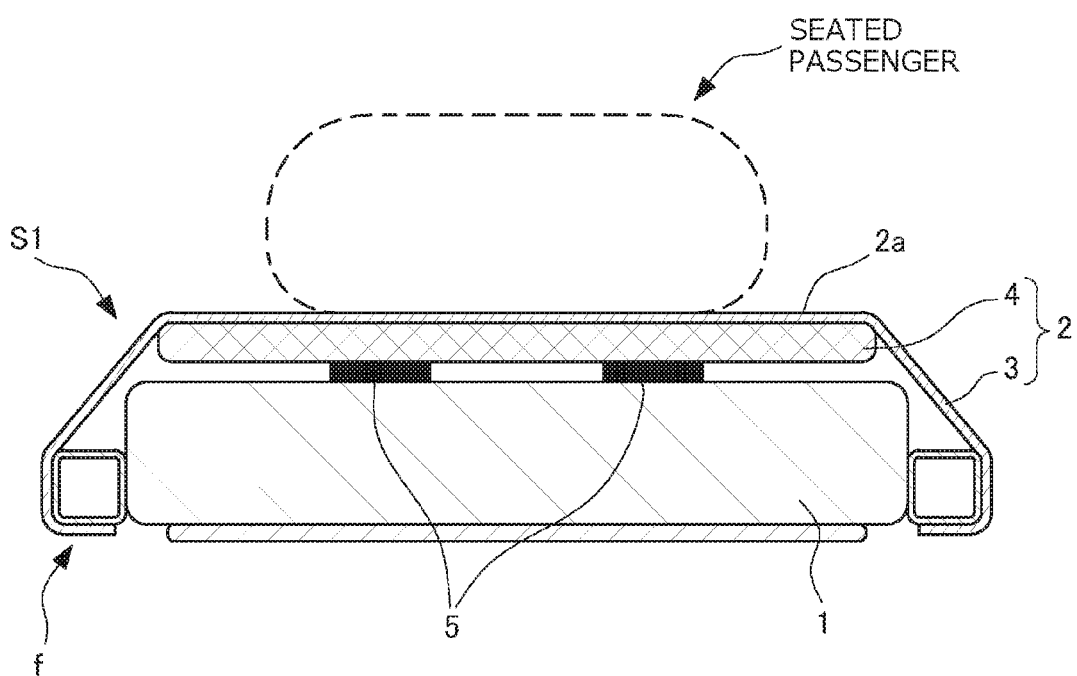
FIG. 2 is a view of the internal structure of the seat according to an embodiment.

As illustrated in FIG. 1, the seat S includes a seat back S1 configured to support a seated occupant from the back side when the occupant is seated. As illustrated in FIG. 2, the seat back S1 includes, as main components, a back frame f forming the framework of the seat back S1, a pad material 1 disposed in front of the back frame f, and a trim cover 2 serving as a cover member configured to cover the back frame f and the pad material 1. FIG. 2 is a view of the internal structure of the seat S, and schematically illustrates a cross section along an A-A line of FIG. 1.

The trim cover 2 has a contact surface 2a for contacting the back of the seated occupant. As illustrated in FIG. 2, the trim cover 2 includes a covering material 3 forming the contact surface 2a, and the wadding material 4 attached to the back surface of the covering material 3 (i.e., the surface of the covering material 3 opposite to the contact surface 2a). The wadding material 4 is made of a material having flexibility, and is interposed between the covering material 3 and the pad material 1 in the thickness direction of the seat back S1. The wadding material 4 is disposed to fit the entirety of the back of the seated occupant in the state in which the back of the seated occupant leans on the seat back S1, for example. Moreover, the wadding material 4 employed for the seat S is made of a foam material with air bubbles communicating with each other, and specifically, is made of a urethane foam material. Note that any materials and any foaming methods may be used for the above-described wadding material 4 without limitations as long as the quality of the vehicle seat can be ensured and the air bubbles communicating with each other can be formed in the wadding material 4.

For the purpose of monitoring the heart rate of the seated occupant, the sensors 5 configured to detect the body potential of the seated occupant are embedded in the seat S. These sensors 5 are capacitive coupling electrode sensors configured to detect the body potential through clothes of the seated occupant and the trim cover 2 without contacting the seated occupant in the state in which the occupant is seated. Note that the configuration of the electrode sensor is not limited, but in the present embodiment, the electrode sensor may be configured such that a thin film made of carbon and a silver strip embedded in the surface of the thin film (i.e., the surface of the thin film facing the trim cover 2) are attached onto a thin plate made of PET. Moreover, each sensor 5 may be a sheet sensor, and as illustrated in FIG. 1, has a substantially-rectangular outer shape as viewed from the front. Each sensor 5 is disposed on the side opposite to the contact surface 2a in the thickness direction of the seat back S1. More specifically, each sensor 5 is disposed between the wadding material 4 and the pad material 1 as illustrated in FIG. 2(a).

Further, the sensors 5 may be arranged in pairs in the right-left direction at positions close to the middle in the width direction of the seat back S1. Particularly in the seat S, four pairs of sensors 5 are arranged in lines in the upper-lower direction of the seat back S1 as illustrated in FIG. 1.

The wadding material 4 is disposed in front of each sensor 5, and the pad material 1 is disposed in back of each sensor 5. In other words, the wadding material 4 has the same number of portions facing the sensors 5 as the number of sensors 5 (eight in the seat S). Arrangement of the sensors 5 according to an embodiment will be described in detail with reference to FIG. 1. The trim cover 2 is divided into upper and lower regions with respect to a groove portion (hereinafter referred to as a "pull-in portion 3a") as a border, the groove portion being formed for pulling the covering material 3 into the trim cover 2. Four sensors 5 are arranged in each of the upper and lower regions. Moreover, as illustrated in FIG. 1, two of four sensors 5 in each region are arranged in the right-left direction, and the remaining two sensors 5 are arranged in the upper-lower direction.

Figure 3:
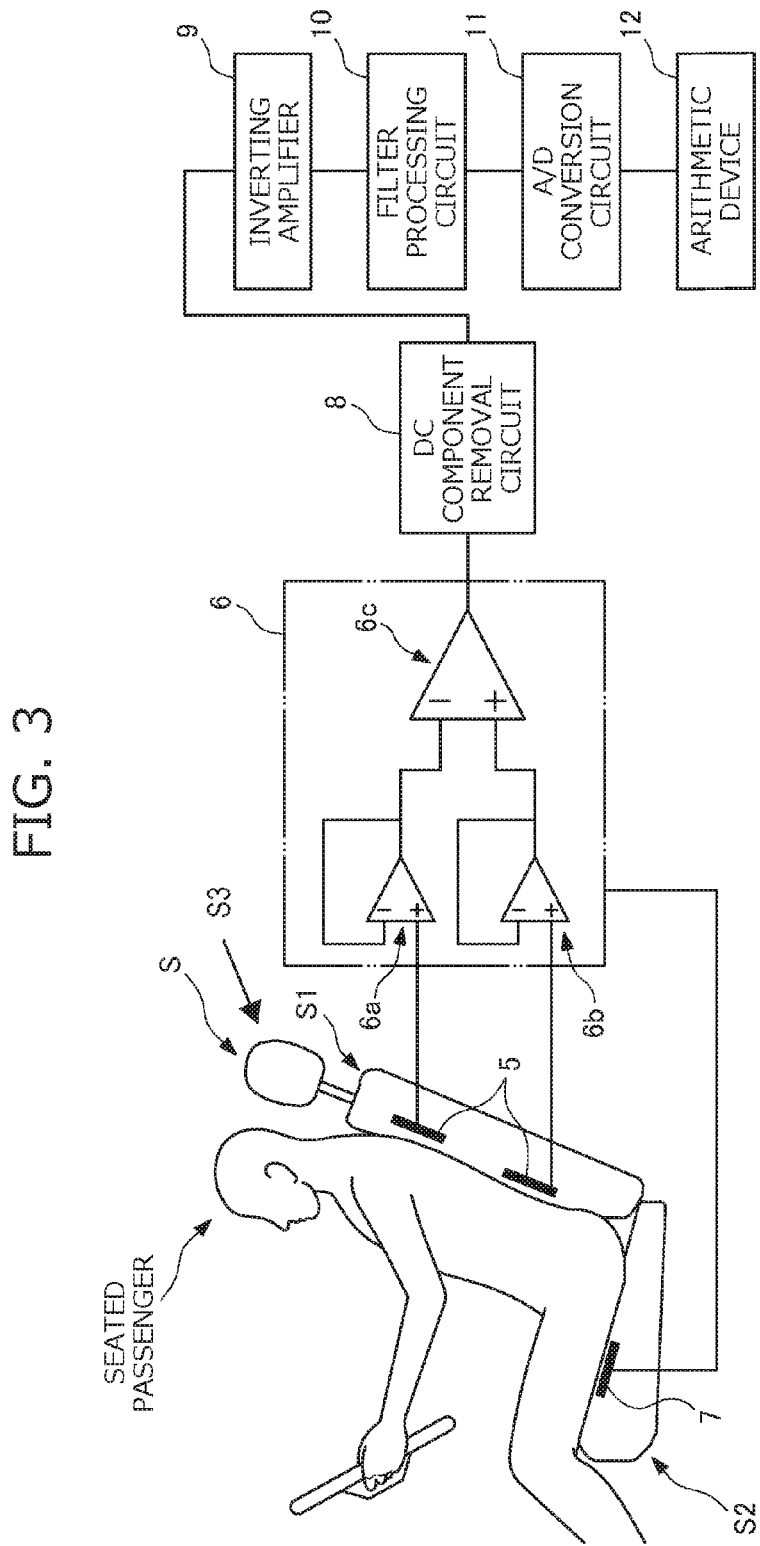
FIG. 3 is a conceptual diagram of a heart rate measurement system using sensors according to an embodiment.

The sensors 5 are connected to a voltage follower 6 illustrated in FIG. 3. When detecting the body potential, the sensors 5 output signals corresponding to the body potential to the voltage follower 6. FIG. 3 is a conceptual diagram of a heart rate measurement system using the sensors 5 embedded in the seat S. Note that in FIG. 3, only two sensors 5 are illustrated for the sake of clarity of description.

The voltage follower 6 includes three operational amplifiers 6a, 6b, 6c. Of theses operational amplifiers, two operational amplifiers 6a, 6b receive signals output from the sensors 5. A signal output from a predetermined sensor 5 is input to one operational amplifier 6a, and a signal output from a sensor 5 paired with the predetermined sensor 5 is input to the other operational amplifier 6b. Then, the operational amplifiers 6a, 6b each amplify the output signal of a corresponding one of the sensors 5 to output the amplified signal to the operational amplifier 6c. The operational amplifier 6c is a differential amplifier. More specifically, the operational amplifier 6c amplifies the difference (the difference signal) between the signals output from both of the operational amplifiers 6a, 6b to output the amplified difference signal.

The voltage follower 6 takes a ground potential as a reference potential, and therefore, an electrode (a ground electrode 7 illustrated in FIG. 3) grounded on the ground is provided at the seat S. The above-described ground electrode 7 is attached to a frame (not shown) of a seat cushion S2 configured to support the hip of the seated occupant, and is electrically connected to a predetermined portion of the voltage follower 6.

The amplified difference signal output from the operational amplifier 6c is input to an arithmetic device 12 by way of a DC component removal circuit 8, an inverting amplifier 9, a filter processing circuit 10 for noise reduction, and an A/D conversion circuit 11. The arithmetic device 12 is configured to execute arithmetic processing for generating waveform data indicating the heart rate waveform of the seated occupant based on the input signal, i.e., the above-described difference signal converted as digital data. With the above-described configuration, a system for measuring the heart rate of the occupant seated on the seat S by using the sensors 5 embedded in the seat S is provided.

The sensors 5 are, as described above, the capacitive coupling sensors configured to detect the body potential of the seated occupant through the clothes of the seated occupant and the trim cover 2, and the detection accuracy thereof depends on the electrostatic capacitance in the open space (the space) between each sensor 5 and the skin of the seated occupant. The space between the sensor 5 and the skin of the seated occupant changes due to a change in the posture of the seated occupant and vibration of the vehicle while the vehicle is running. Due to such a space change, the above-described electrostatic capacitance changes. When the above-described space changes such that the electrostatic capacitance decreases, the accuracy in body potential detection by the sensors 5 is lowered.

For this reason, each portion of the trim cover 2 facing a corresponding one of the sensors 5 in the seat S contains a dielectric configured to increase the dielectric constant of such a portion to ensure the electrostatic capacitance at a relatively-high level. Specifically, titanium oxide, particularly rutile type titanium oxide, as the dielectric is contained across the entirety of the portions, facing the sensors 5, of the wadding material 4 provided on the back side of the covering material 3 of the trim cover 2. The portions of the wadding material 4 facing the sensors 5 are portions positioned right in front of the rectangular sensors 5, and there are eight portions in the seat S. That is, each facing portion has the substantially same outer edge as the outer edge of a corresponding one of the sensors 5, and is positioned at the same position as a corresponding one of the sensors 5 in the upper-lower direction and the width direction of the seat back S1.

Note that in the seat S, the titanium oxide is contained across the entirety of the wadding material 4 including the portions facing the sensors 5. In other words, in the seat S, the surface size of the portion of the trim cover 2 containing the titanium oxide on the side facing the sensor 5 is larger than the surface size of the sensor 5 on the side facing the trim cover 2. With this configuration, the electrostatic capacitance between each sensor 5 and the skin of the seated occupant can be effectively increased. As a result, the accuracy in detection of the body potential of the seated occupant by each sensor 5 is further improved.

In the seat S, the sensors 5 are arranged, and the titanium oxide is contained across the entirety of the wadding material 4 including the portions facing the sensors 5, as described above. That is, the portions of the trim cover 2 containing the titanium oxide face all of the sensors 5, and are continuously provided. Thus, in the seat S, the portions of the trim cover 2 containing the titanium oxide are provided as a united member. With this configuration, the portion of the trim cover 2 containing the titanium oxide can be easily provided at the seat S.

Examples of the method for containing the titanium oxide in the wadding material 4 include the method in which after a wadding material 4 foam-molded in advance is dipped in a liquid mixture of fine powder of titanium oxide and liquid such as water, the wadding material 4 is dried. By such a method, air bubbles formed in the wadding material 4 are impregnated with the fine powder of the titanium oxide, and therefore, the titanium oxide can be effectively contained in the wadding material 4.

Moreover, in the seat S, the air bubbles formed in the wadding material 4 are the air bubbles communicating with each other. Thus, the air bubbles can be easily impregnated with the titanium oxide. As a result, the wadding material 4 can be obtained with a relatively-high titanium oxide content.

In the seat S configured such that the portions of the wadding material 4 facing the sensors 5 contain the titanium oxide as described above, the dielectric constant of such portions increases, and therefore, the electrostatic capacitance in the space between each sensor 5 and the skin of the seated occupant is improved. As a result, in the seat S, the accuracy in detection of the body potential of the seated occupant by the sensors 5 is improved as compared to a conventional seat configured such that sensors 5 are embedded.

More specifically, the titanium oxide is contained in the portions of the wadding material 4 facing the sensors 5, and therefore, the dielectric constant increases as compared to the case of containing no titanium oxide. Moreover, the electrostatic capacitance in the space between each sensor 5 and the skin of the seated occupant increases in proportion to the above-described dielectric constant. Since the portions of the wadding material 4 facing the sensors 5 contain the titanium oxide, the electrostatic capacitance in the seat S exhibits a value much greater than the electrostatic capacitance in the conventional seat containing no titanium oxide. Specifically, when the size of each sensor 5 is set at a predetermined size and measurement is made under a temperature of 25° C. and a humidity of 50%, the electrostatic capacitance in the case of containing the titanium oxide in the wadding material 4 increases to several times (e.g., about three times) as high as the electrostatic capacitance in the case of containing no titanium oxide.

In the seat S, the titanium oxide is contained in the wadding material 4 to increase the electrostatic capacitance, as described above. More specifically, the air bubbles of the wadding material 4 are impregnated with the fine powder of the titanium oxide. With such a configuration, the flexibility of the wadding material 4 can be maintained while the electrostatic capacitance can be increased. With the configuration of the seat S, the sense of seating on the seat S (i.e., the comfortability on the seat S) can be maintained while the detection accuracy of the sensors 5 can be improved. As a result, a comfortable sense of seating can be provided to the occupant seated on the seat S, and the heart rate of the seated occupant can be stably measured.

An embodiment of a seat has been described above. However, the above-described embodiment is a non-limiting example for understanding the seat. Change and modification can be made to the invention without departing from the disclosure, and the invention includes equivalents thereof.

In the above-described embodiment, the rutile type titanium oxide may be contained in the wadding material 4. However, the invention is not limited to the rutile type titanium oxide. Anatase type titanium oxide may be contained. Further, barium titanate is also effective as a dielectric other than the titanium oxide. That is, the barium titanate may be contained in the portions of the wadding material 4 facing the sensors 5.

A material other than the titanium oxide and the barium titanate may be used as long as such a dielectric can be contained in the above-described facing portions to increase the dielectric constant of such portions. Note that in order to stably detect the body potential by the sensors 5, a material being capable of increasing the dielectric constant in the portions facing the sensors 5 to 10 to 30 (F/m) and having a relatively-high specific permittivity is preferred.

In the above-described embodiment, examples of the method for forming the wadding material 4 containing the titanium oxide include the following method: the wadding material 4 is dipped in the liquid containing the fine powder of the titanium oxide and is dried, and as a result, the wadding material 4 is impregnated with the titanium oxide. However, the method for forming the wadding material 4 containing the titanium oxide is not limited to such a method. For example, fine powder of titanium oxide or barium titanate may be sprayed onto a wadding material 4 foam-molded in advance. According to such a method, the wadding material 4 can partially contain the titanium oxide or the barium titanate. Thus, the above-described dielectric can be contained only in the portions facing the sensors 5 in the state in which the sensors 5 are embedded in the seat back S1, for example.

Alternately, a wadding material 4 containing the above-described dielectric may be formed in the following manner: fine powder of titanium oxide or barium titanate is pre-mixed with a urethane base material as a base material of the wadding material 4, and then, the urethane base material is foamed.

In the above-described embodiment, the wadding material 4 formed with the air bubbles communicating with each other is used. However, the present invention is not limited to such a wadding material 4. A wadding material 4 formed with air bubbles isolated from each other may be used. Note that with the wadding material 4 formed with the air bubbles communicating with each other, the titanium oxide or the barium titanate can be easily contained in the air bubbles, and the content thereof is relatively high. This can more easily improve the detection accuracy of the sensors 5. On such a point, the wadding material 4 formed with the air bubbles communicating with each other is suitable according to an embodiment.

Figure 4:
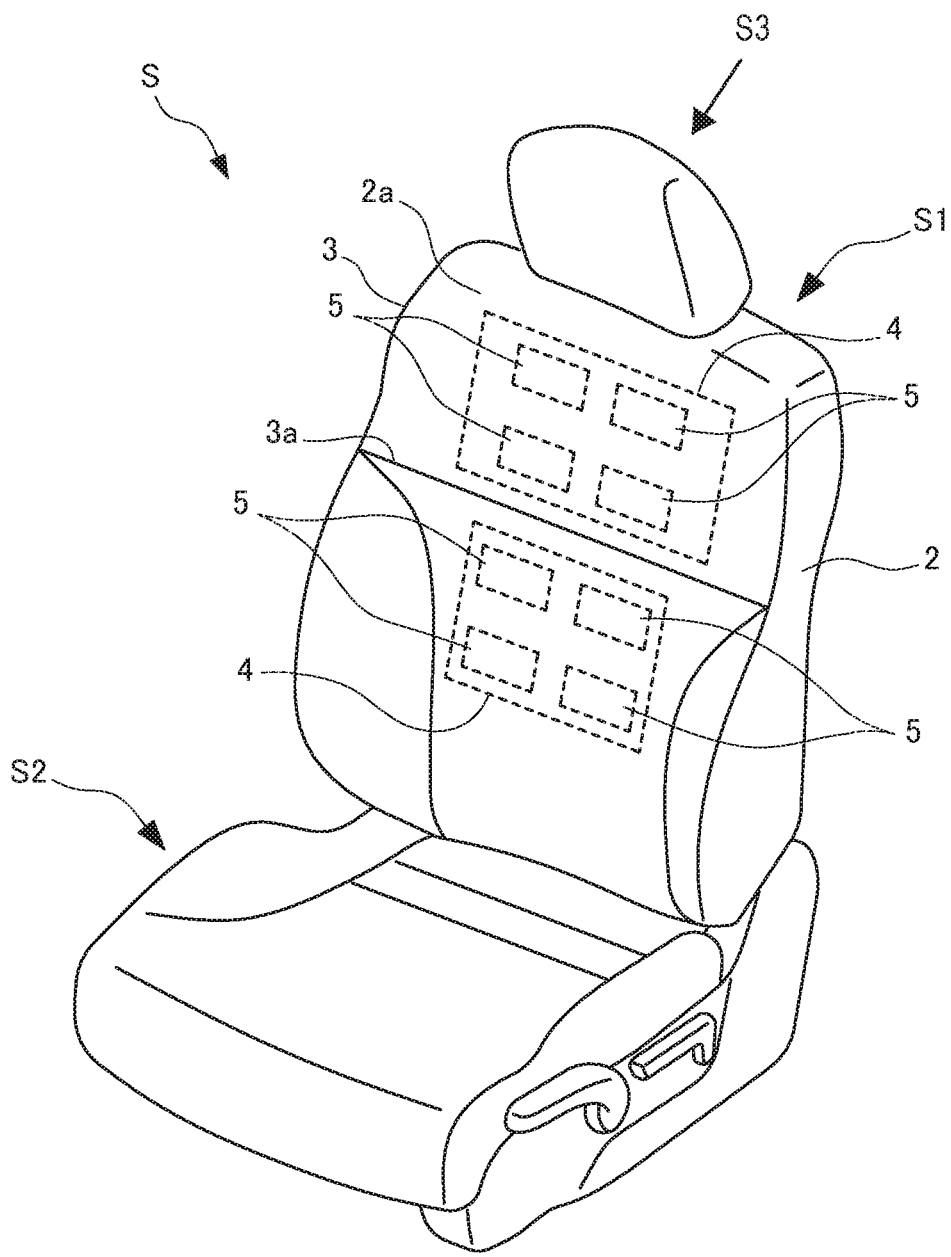
FIG. 4 is a view of a variation of arrangement of portions of a cover member containing a dielectric.

The portions of the wadding material 4 facing the sensors 5 may be molded as a single member, and may be provided to cross over the pull-in portion 3a of the trim cover 2. Alternatively, the wadding material 4, exactly the wadding material 4 containing the titanium oxide, may be provided with the wadding material 4 being divided into upper and lower pieces with respect to the pull-in portion 3a as the border, as illustrated in FIG. 4. FIG. 4 is a view of a variation of arrangement of the pieces of the wadding material 4 containing the titanium oxide.

Since the wadding material 4 containing the titanium oxide is divided into plural pieces as illustrated in FIG. 4, the size of each piece of the wadding material 4 is reduced, and therefore, each piece of the wadding material 4 is more easily attached. When the pieces of the wadding material 4 are arranged to sandwich the pull-in portion 3a in the upper-lower direction as illustrated in FIG. 4, such arrangement is less susceptible to the pull-in portion 3a as compared to the case where the wadding material 4 crosses over the pull-in portion 3a, and the wadding material 4 can be attached in a favorable state. On the other hand, in the case where the wadding material 4 containing the titanium oxide is not divided into pieces, but is used as a single member, the number of components can be reduced.

In the above-described embodiment, the configuration in which the wadding material 4 of the trim cover 2 contains the titanium oxide as the dielectric has been described. Note that the configuration in which the trim cover 2 contains the dielectric is not limited to the above-described configuration, and other configurations (hereinafter referred to as "variations") are conceivable. The variations may include the configuration in which an attachment member 20 containing a dielectric such as titanium oxide is attached to at least part of portions of a trim cover 2 facing sensors 5.

More specifically, the attachment member 20 containing the titanium oxide is attached to a corresponding one of the portions of the trim cover 2 facing the sensors 5. The attachment member 20 is formed of a sheet made of silicon rubber, and has flexibility. The attachment member 20 is provided separately for the portions facing the sensors 5. In other words, the above-described attachment member 20 is provided for each sensor 5, and is disposed at the position (the front position) facing each sensor 5.

Figure 5:
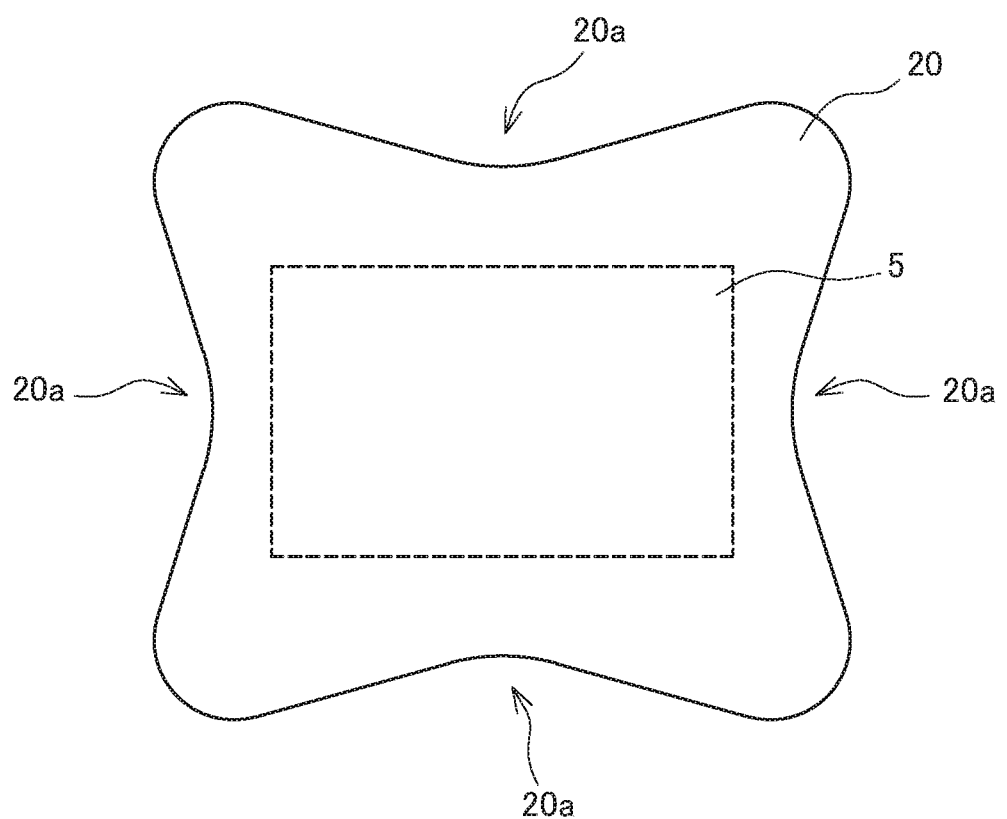
FIG. 5 is a view of an attachment member used for a seat of a variation.

The configuration of the attachment member 20 will be described. As illustrated in FIG. 5, the surface size of the attachment member 20 on the side facing the sensor 5 is larger than the surface size of the sensor 5 on the side facing the trim cover 2. This can effectively increase the electrostatic capacitance between each sensor 5 and the skin of the seated occupant. As a result, the accuracy in detection of the body potential of the seated occupant by each sensor 5 is further improved. FIG. 5 is a view of the attachment member 20 used for a seat of a variation. Note that in FIG. 5, the sensor 5 is indicated by a dashed line to show the position relationship between the attachment member 20 and the sensor 5.

Moreover, the shape of the attachment member 20 will be described. As illustrated in FIG. 5, the attachment member 20 has such a substantially-rectangular outer appearance that a middle portion of each of four sides is cut out in a triangular shape. A cutout 20a is formed on each side of the attachment member 20. Thus, when the back of the seated occupant leans on a seat S to bend the trim cover 2, the attachment member 20 can be easily bent to follow bending of the trim cover 2. That is, the attachment member 20 made of the silicon rubber flexibly deforms under a load acting on the attachment member 20 every time the back of the seated occupant leans on the seat, and as a result, the durability against such a load can be improved.

The above-described advantageous effects can be more effectively exhibited by the cutouts 20a formed on all of the four sides of the substantially-rectangular attachment member 20. Note that at least one cutout 20a may be formed, or the cutout 20a may be formed only on one of the four sides of the attachment member 20.

In the above-described embodiments, the titanium oxide is contained across the entirety of the wadding material 4. In order to provide the advantageous effects, the titanium oxide or the barium titanate may be contained in at least part of the portions of the wadding material 4 facing the sensors 5. Note that in order to effectively provide the advantageous effects, the titanium oxide or the barium titanate is preferably contained across the entirety of the portions facing the sensors 5.

Any of the embodiments described above is configured to include the dielectric in the trim cover 2 (specifically the wadding material 4 or the attachment member 20), but may include the dielectric in the portions of the seat facing the sensors 5. That is, the portions of the seat including the dielectric may be portions other than the trim cover 2. An example will be described. In the above-described embodiments, the attachment member 20 containing the titanium oxide is attached to each portion of the trim cover 2 facing a corresponding one of the sensors 5. Note that the invention is not limited to such a configuration, and the above-described attachment member 20 may be attached to the surface (hereinafter referred to as the "surface close to the trim cover 2") of a corresponding one of the sensors 5 facing the trim cover 2.

Figure 6:
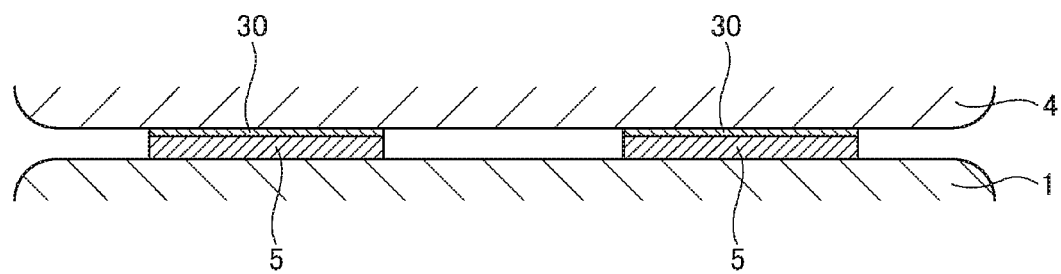
FIG. 6 is a cross-sectional view of sensors in a seat of a second variation.
Figure 7:
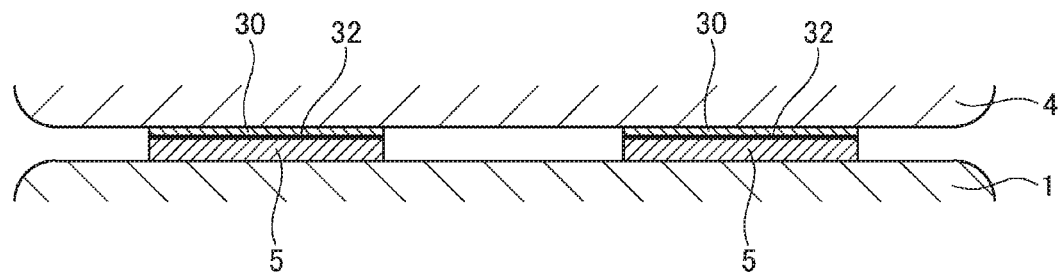
FIG. 7 is a cross-sectional view of sensors in a seat of a third variation.

Other configurations in which a portion other than the trim cover 2 includes a dielectric are possible, and examples of such a configuration include the configurations illustrated in FIGS. 6 and 7. Any of the configurations illustrated in FIGS. 6 and 7 is the configuration in which a portion including a dielectric is provided on the surface of each sensor 5 close to a trim cover 2. The configuration illustrated in FIG. 6 will be described. Paste or ink (equivalent to an application agent) containing barium titanate as a dielectric is applied onto the surface of each sensor 5 close to the trim cover 2 to form an application agent layer 30. Note that the paste or the ink may be applied onto at least part of the surface of each sensor 5 close to the trim cover 2, and may be applied in a dot pattern or a grid pattern.

The configuration illustrated in FIG. 7 will be described. A film 31 containing barium titanate as a high dielectric is attached to the surface of each sensor 5 close to a trim cover 2. The film 31 is attached to the surface of each sensor 5 close to the trim cover 2 through a conductive double-faced tape 32. Note that the film 31 may be attached to at least part of the surface of each sensor 5 close to the trim cover 2, and may be attached in a dot pattern or a grid pattern.

In the configurations described above, i.e., the configuration in which each portion including the dielectric is directly provided on the surface of a corresponding one of the sensors 5 close to the trim cover 2 and is integrated with the corresponding one of the sensors 5, the flexibility of the sensor 5 is more easily ensured as compared to the configuration in which each portion including a dielectric is separated from a corresponding one of sensors 5 (e.g., the configuration in which each portion including a dielectric is provided at a trim cover 2). Specifically, in the configuration in which each portion including the dielectric is integrated with a corresponding one of the sensors 5, the portion including the dielectric easily follows deformation of the corresponding one of the sensors 5. That is, when the occupant seated on the seat S leans on the seat back S1, and then, a load acts on the sensors 5, the integrated portions of the sensors 5 and the portions including the dielectric freely deform under the load to exhibit favorable followability.

In the above-described embodiments, the vehicle seat has been described by way of example. However, the invention is not limited to the vehicle seat, but may include seats used for purposes other than mounting on vehicles, such as seats placed in facilities such as movie theaters. Due to a change in the posture of a seated occupant or vibration of a vehicle while the vehicle is running, the electrostatic capacitance between the skin of the seated occupant and each sensor changes. As a result, there is a probability that the electrostatic capacitance decreases. For vehicle seats, the sense of seating on the seat (the comfortability on the seat) is focused as the quality of these seats. For this reason, the advantageous effects of maintaining the sense and comfort of seating on the seat and improving the detection accuracy of the sensors.

REFERENCE SIGNS LIST

1: pad material
2: trim cover (cover member)
2*a*: contact surface
3: covering material
3*a*: pull-in portion
4: wadding material
5: sensor
6: voltage follower
6*a*, 6*b*, 6*c*: operational amplifier
7: ground electrode
8: DC component removal circuit
9: inverting amplifier
10: filter processing circuit
11: A/D conversion circuit
12: arithmetic device
20: attachment member
20*a*: cutout
30: application agent layer
31: film
32: double-faced tape
S: seat
S1: seat back
S2: seat cushion
S3: head supporting portion
f: back frame

The invention claimed is:

1. A seat comprising:
   a cover member having a contact surface for a seated occupant; and
   a capacitive coupling sensor disposed opposite to the contact surface and configured to detect through the cover member, when the seated occupant is seated, a body potential of the seated occupant, and to output a signal corresponding to the body potential, and
   wherein an application agent is applied onto at least part of a surface of the sensor facing the cover member to form an application agent layer, and contains a dielectric to increase a dielectric constant of the application agent layer.

2. The seat according to claim 1, wherein the dielectric is titanium oxide or barium titanate.

3. The seat according to claim 1, wherein the seat is mounted on a vehicle.

4. The seat according to claim 1, further comprising a head supporting portion which supports a head of the seated occupant;
   wherein the application agent layer is located below the head supporting portion.

5. The seat according to claim 1, further comprising a pad material covered by the cover member;
   wherein the sensor is arranged between the cover member and the pad material, and
   the application agent layer is arranged at a position closer to the cover member than the pad material.

6. A seat comprising:
   a cover member having a contact surface for a seated occupant; and
   a capacitive coupling sensor disposed opposite to the contact surface and configured to detect through the cover member, when the seated occupant is seated, a body potential of the seated occupant, and to output a signal corresponding to the body potential, and
   wherein the cover member comprises:
      a covering material forming the contact surface, and
      a wadding material attached to a surface of the covering material opposite to the contact surface; and
   a dielectric to increase a dielectric constant of the wadding material is contained in at least part of a portion of the wadding material facing the sensor.

7. The seat according to claim 6, wherein the wadding material comprises a foam material formed with air bubbles communicating with each other.

8. The seat according to claim 6, wherein
the sensor is a sheet sensor, and
an outer edge of the sensor is located on an inside of an outer edge of the wadding material.

9. The seat according to claim 6, wherein
the sensor comprises a plurality of arranged sensors, and
the wadding material faces at least two of the sensors, and is continuously provided.

10. The seat according to claim 6, wherein the dielectric is titanium oxide or barium titanate.

11. The seat according to claim 6, wherein the seat is mounted on a vehicle.

12. The seat according to claim 6, further comprising a head supporting portion which supports a head of the seated occupant;
wherein the wadding material is located below the head supporting portion.

13. The seat according to claim 6, further comprising a pad material covered by the cover member;
wherein the sensor is arranged between the cover member and the pad material, and
the wadding material is arranged at a position closer to the cover member than the pad material.

14. A seat comprising:
a cover member having a contact surface for a seated occupant; and
a capacitive coupling sensor disposed opposite to the contact surface and configured to detect through the cover member, when the seated occupant is seated, a body potential of the seated occupant, and to output a signal corresponding to the body potential, and
wherein an attachment member containing a dielectric to increase a dielectric constant of the attachment member is attached to at least part of a portion of the cover member facing the sensor.

15. The seat according to claim 14, wherein
at least one cutout is provided in an outer edge of the attachment member, the cutout extending inward from the outer edge.

16. The seat according to claim 14, wherein
the sensor is a sheet sensor, and
an outer edge of the sensor is located on inside of an outer edge of the attachment member.

17. The seat according to claim 14, wherein the dielectric is titanium oxide or barium titanate.

18. The seat according to claim 14, wherein the seat is mounted on a vehicle.

19. The seat according to claim 14, further comprising a head supporting portion which supports a head of the seated occupant;
wherein the attachment member is located below the head supporting portion.

20. The seat according to claim 14, further comprising a pad material covered by the cover member;
wherein the sensor is arranged between the cover member and the pad material, and
the attachment member is arranged at a position closer to the cover member than the pad material.

* * * * *